United States Patent

Yeh

[11] Patent Number: 5,725,373
[45] Date of Patent: Mar. 10, 1998

[54] PERIODONTAL PROBE TIP FOR DIAGNOSING PERIODONTITIS AND DENTAL DECAY

[76] Inventor: Richard T. Yeh, 13572 Montague St., Arleta, Calif. 91331

[21] Appl. No.: 682,275

[22] Filed: Jul. 17, 1996

[51] Int. Cl.⁶ .................................................. A61C 19/04
[52] U.S. Cl. ........................................ 433/72; 433/215
[58] Field of Search .................. 433/72, 215; 128/776, 128/777

[56] References Cited

U.S. PATENT DOCUMENTS

| | | | |
|---|---|---|---|
| 4,447,206 | 5/1984 | Ushiyama | 128/776 |
| 4,886,454 | 12/1989 | Loewenthal et al. | 433/72 |
| 5,096,420 | 3/1992 | Loewenthal | 433/72 |
| 5,178,537 | 1/1993 | Currie | 433/72 |
| 5,244,386 | 9/1993 | Angelo, Jr. | 433/72 |
| 5,244,387 | 9/1993 | Fuierer | 433/72 |
| 5,327,903 | 7/1994 | Lindskog et al. | 433/72 |
| 5,423,677 | 6/1995 | Brahesami | 433/72 |
| 5,516,285 | 5/1996 | Yacker et al. | 433/72 |

*Primary Examiner*—Paul J. Hirsch

[57] ABSTRACT

A periodontal probe tip 14 is made of strong flexible plastic with thermochromatic plastic ingredient and litmus test paper band. Probe tip 14 is an indicator for measuring the depth of periodontal pocket and for sensing gum temperature increasing and sensing acidity around tooth. Probe tip 14 will show color change to indicate gum disease and tooth decay initiating the disease process. People will have time to interrupt the disease process and on to better oral health.

4 Claims, 1 Drawing Sheet

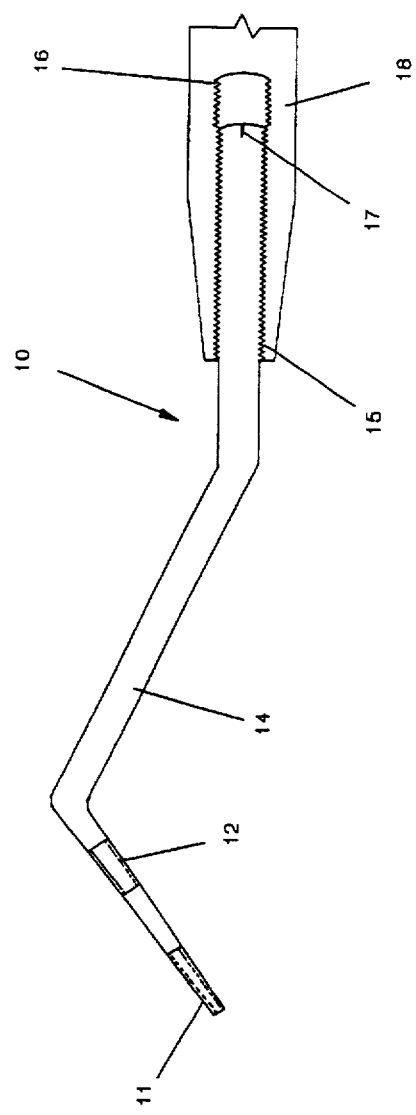
Fig. 1
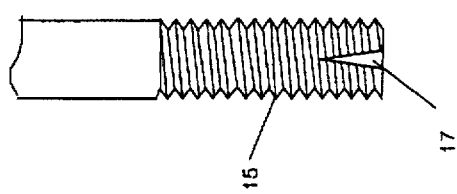
Fig. 3
Fig. 2

PERIODONTAL PROBE TIP FOR DIAGNOSING PERIODONTITIS AND DENTAL DECAY

FIELD OF INVENTION

The present invention relates to a periodontal probe and is particularly directed to a periodontal probe tip which is diagnosing periodontitis and tooth decay in the very early stages by color change.

PRIOR ART

Gum disease and tooth decay are caused by bacterial invasion which result in decompostion of bone around tooth and tooth infection, if left untreated.

Gum disease and tooth decay can be prevented by good oral hygiene and be treated. The treatment will mainly be directed to interrupt the progress of the disease.

There are more than three quarters of American adults having gum disease and more than half of American adults having tooth decay experience.

Gum disease and tooth decay are initial diseases which lack of symptoms. However, the dentist can see early signs of an incipient disease development by regular checkup exams. In U.S. Pat. No. 5,327,903 it employed temperature differences between the bottom of the periodontal pocket and the mouth floor to detect the periodontal inflammation.

Because the device is made of thermoelement and semiconductor, it is too expensive and sophisticated. Another disadvantage of this prior art is that the device is so sensitive to very small range of temperature change which will cause some false positive and false negative responses when the patients drink hot coffee or ice tea prior to their checkup exams. One more disadvantage of this prior art is the device can not detect tooth decay in the very early stage. Traditionally, dentist diagnoses tooth decay by reading X-Ray film to determine whether the tooth has been demineralized or not. Sometimes dentists use a dental explorer to detect cavity. Usually there must be at least twenty percent of mineral loss, then the dentist can read the X-Ray film to assure there is decay or bone loss of the tooth. From a preventive dentistry view, it is late to find out the disease has already happened. As we know, gum disease and tooth decay are caused by bacteria. Because bacteria produce acid which will wash away tooth mineral and bone mineral, tooth and bone initiate demineralization and eventualy lead to large cavity and bone loss. If we can detect acidity around tooth in the very early stages, we can prevent both tooth decay and gum diseases.

SUMMARY OF THE INVENTION

These disadvantages of the prior art and traditional exams are overcomed with the present invention. An improved periodontal probe tip which can detect gum inflammation by periodontal probe tip color change due to the fact that temperature increases from gum inflammation. An improved probe tip requires no expensive and sophisticated device. These advantages of the present invention are preferably attained by providing an improved periodontal probe tip having an acid detecting litmus in the test paper band unit which releasably attachable to the probe tip free end side. While examining, the probe tip detects acid produced by bacteria which habituate around tooth.

The temperature change and acidity detection are used as an indicator of bacterial activity around tooth.

Accordingly, one of the present invention is to provide an improved periodontal probe tip, which is disposable to prevent cross contamination.

Another object of the present invention is to provide an improved periodontal probe tip whose color change will start above 100 degrees Fahrenheit temperature that will prevent misleading results.

A specific object of the present invention is to provide an improved periodontal probe tip having a color change due to thermal increasing and an acidity detecting paper band and simultaneously measuring periodontal pocket depth. These data will guide the dentist to diagnose oral disease in the very early stage.

These and other objects of the present invention will be apparent from the following detailed description taken with reference to the figures of the accompanying drawings.

BRIEF DESCRIPTION OF DRAWING

FIG. 1 is a periodontal probe

FIG. 2 is a periodontal probe tip free end enlarged detail

FIG. 3 is a periodontal probe tip detachable end enlarged detail.

DESCRIPTION OF PREFERRED EMBODIMENT

Referring now to FIG. 1, there is shown a periodontal probe 10 comprising a handle 18 and a periodonal probe tip 14. Periodontal probe tip 14 is made of strong flexible plastic (e.g. polypropylene) with thermochromatic plastic ingredient which will change color when the temperature is above 100 degree Fahrenheit.

If the dentist checks the inflammatory gum, probe tip 14 contacts the inflammatory gum and probe tip 14 will start to change color. Then the dentist can show the patient there is some kind of gum disease occurring in their mouth. If the dentist checks the normal gum, probe tip 14 contacts the normal gum and probe tip 14 will not change color. Probe tip 14 comprises of litmus test paper band 12 for detecting acid which bacteria produce, causing tooth and bone demineralization. When the dentist checks, the litmus test paper will show color change. The dentist can show the patient there is too much acid around tooth leading to tooth decay and bone loss around tooth. A detachable end 15 to connect handle 18 by a thread fitting 16. Also at detachable end 15 bottom third has a split 17 which will prevent probe tip 14 to become loose. Fitting 16 joining the forward and a detachable end 15 of peridontal probe tip 14 comprising of male and female thread members.

Referring now to FIGS. 2 and 3, probe tip 14, a detachable end 15, enlarged detail show split 17 and free end 11 section part 13 is a 3 mm long accordingly for measuring of periodontal pocket depth.

Probe tip 14 can obtain periodontal pocket depth measurement, gum inflammation and acid detection around tooth at the very early stage that will lead to interrupt the disease process.

I claim:

1. A process for diagnosing condition related to gum disease and tooth decay based on conditions around a tooth, comprising:
   a) measuring a distance between the bottom and the mouth of a periodontal pocket,
   b) sensing a temperature difference between the bottom and the mouth of the periodontal pocket,
   c) sensing acidity which bacteria produces around said tooth demineralizing tooth and bone to cause tooth decay and bone loss,
   d) determining the degree and development of gum disease and tooth decay based on the measurements taken under step (a), step (b), and step (c).

2. A process for diagnosing an inflammation condition related to gum disease and acidity condition related to tooth decay add bone loss around said tooth based on conditions around said periodontal pocket according claim 1, further comprising the step of establishing the stage of activity of said gum disease and tooth decay based on the evaluation of said determining step.

3. Apparatus for diagnosing an inflammation related to gum disease and tooth decay comprising:

a periodontal probe tip having, a means for measuring periodontal pocket depth by a graduated scale, a means for sensing a temperature increase by periodontal tip chromatic change, a means for sensing acidity by a periodontal probe tip end paper band color change, whereby bacterial activity is determined by measuring periodontal pocket depth, sensing the temperature change between the bottom and the mouth of the periodontal pocket, and sensing the acidity around a tooth.

4. Apparatus according to claim 3, wherein said periodontal probe tip is disposable and made of strong flexible thermochromatic plastic material, and further includes a litmus test paper band.

* * * * *